United States Patent [19]
Gerard et al.

[11] Patent Number: 4,826,861

[45] Date of Patent: May 2, 1989

[54] NOVEL HETEROCYCLIC COMPOUNDS SUBSTITUTED WITH AN AMINO GROUP, THEIR PROCESSES OF MANUFACTURE AND THE PHARMACEUTICAL COMPOSITIONS CONTAINING THEM

[75] Inventors: Moinet Gerard, Orsay; Schaefer Michel, Chilly Mazarin, both of France

[73] Assignee: Albert Roland, S.A., Paris, France

[21] Appl. No.: 1,516

[22] Filed: Jan. 7, 1987

Related U.S. Application Data

[63] Continuation of Ser. No. 564,918, Dec. 23, 1983, Pat. No. 4,647,557.

[30] Foreign Application Priority Data

Dec. 28, 1982 [CH] Switzerland .................... 7591/82

[51] Int. Cl.$^4$ .................................... C07D 277/18

[52] U.S. Cl. .................................... 514/371; 514/370; 548/193; 548/195; 548/196

[58] Field of Search ............... 548/163, 164, 161, 193, 548/195, 196; 514/371, 365, 370

[56] References Cited

PUBLICATIONS

Copy of Structural Printout of Cas-On-Line Data Base Search
Chemical Abstracts 84(3):17212c; 1976.
Chemical Abstracts 73(17):87827d; 1970.
Chemical Abstracts 72(19):100579a; 1970

*Primary Examiner*—C. Warren Ivy
*Attorney, Agent, or Firm*—Omri M. Behr

[57] ABSTRACT

This invention relates to 2-aminothiazoles and to their process of manufacture. These compounds are endowed with potent antimicrobial and antifungic properties. They are useful in antibacterial and antifungal therapy.

7 Claims, No Drawings

NOVEL HETEROCYCLIC COMPOUNDS SUBSTITUTED WITH AN AMINO GROUP, THEIR PROCESSES OF MANUFACTURE AND THE PHARMACEUTICAL COMPOSITIONS CONTAINING THEM

This application is continuating application to patent application Ser. No. 564 918 filed on Dec. 23, 1983 by the same assignors and now U.S. Pat. No. 4,647,557.

PRIOR ART

The prior art may be illustrated by the following references.
GILMAN U.S. Pat. No. 4,165,378
GILMAN U.S. Pat. No. 4,347,370

SUMMARY OF THE INVENTION

This invention relates to 4-aryl-2-aminothiazoles of formula I:

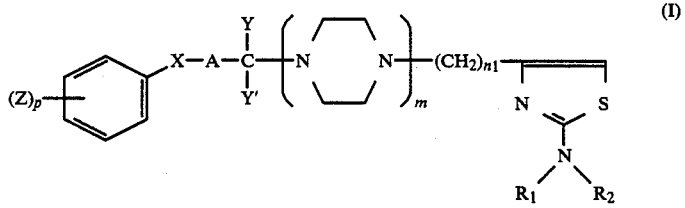

wherein Z, X, A, Y, Y', $R_1$, $R_2$, p, m and n have the meanings given in the specification.

They are produced according to a process which consists in reacting a αhalogeno ketone with thio urea in an inert solvent to produce the free aminothiazole which is further acylated with a functional derivative of a carbonic, sulphonic or carboxylic acid.

The resulting 2-amino-4-arylthiazoles have antibacterial and antifungal properties namely against pathogenic strains. They are of value for the treatment of bacterial or fungal diseases in human or veterinary therapy in the form of pharmaceutical compositions.

This invention relates to novel heterocyclic derivatives bearings an amino group and to process for making said compounds.

More particularly this invention provides novel heterocyclic compounds and hetero ring of which has two hetero-atoms the same or different, substituted with a free or substituted amino group.

Specifically this invention provides the compounds having the formula I:

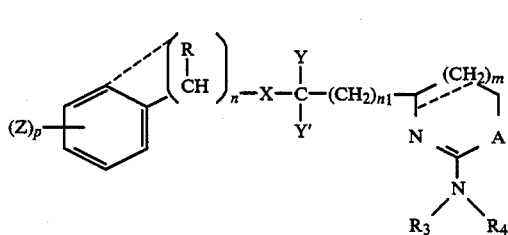

wherein:
Z is a hydrogen, a halogen, a lower alkyl radical, a lower alkoxy radical, a trifluoromethyl, a trifluoromethoxy, a cyano group, a nitro group, a carboxamido group, a lower alkenyl radical, a lover alkylthio, a lower alkyne dioxy, a lower cyclo alkenyl radical or a lower cycloalkyl radical;

X is an oxygen, a sulphur atom or an imino group of the formula >N—$R_1$ where $R_1$ is a hydrogen, a lower alkyl radical, an acyl residue derived from an organic carboxylic or sulphonic acid; a methylene group or a direct bond;

Y is a hydrogen, a lower alkyl radical, a phenyl radical, a substituted phenyl radical, a hydroxy or a phenoxy radical;

Y' is a hydrogen, or Y and Y' together are an oxygen, or Y forms with the adjacent phenyl ring, when R is zero, a bicyclic- homo- or heterocyclic, saturated or unsaturated structure;

A is a group NH or a sulphur atom;

$R_3$ and $R_4$ the same or different, are hydrogen, a lower alkyl radical, a lower alkenyl radical, an aryl lower alkyl radical, a heteroaryl lower alkyl radical, an aryl, an alcoyloxycarbonyl group, an acyl residue from an organic carboxylic acid having from 1 to 10 carbon atoms or an amino group;

or $R_3$ and $R_4$ together form with the nitrogen atom to which they are bound, an alkylene chain optionally including one or two extra hetero atoms;

R is a hydrogen, a lower alkyl radical, a phenyl radical which may be substituted or a phenylene radical linked to the adjacent phenyl ring by an alkylene chain having 1 or 2 carbon atoms;

n is zero or 1;

$n_1$ is zero, 1 or 2;

m is zero, 1 or 2, p is 1, 2 or 3, and the dotted line symbolizes an optional carbon-carbon double bond.

This invention also provides the acid addition salts thereof with a mineral or organic acid, preferably a therapeutically compatible acid. This invention further includes the tautomeric imino forms of the compounds of formula I. Due to the delocalization of the intracyclic double bond in the nitrogenous ring, the compounds of formula I, in which at least one of the substituents $R_3$ and $R_4$ are hydrogen, may be represented in the form of an imino derivative having the formula I':

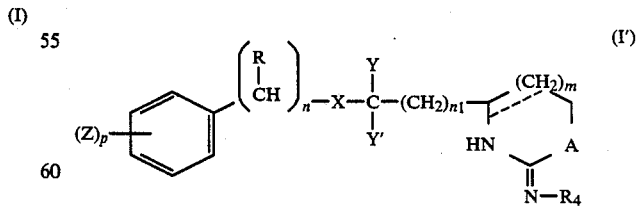

in which the substituents Z, p, R, X, Y, Y', $R_4$, n, m and $n_1$ remain defined as above-given.

The amino (I) form and the imino (I') form may coexist at the same time or the two tautomeric forms may be obtained distinctly either in the free form or in the salified form. This invention also provides to the optically-active isomers of a compound of formula I when containing at least one chiral atom, namely when Y and Y' are different.

Among the compounds of formula I they may more precisely be cited: the compounds having the formula I":

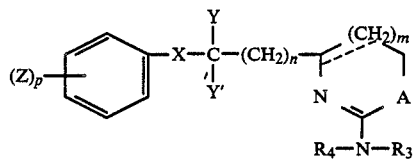

which correspond to the case where n is zero and X is oxygen, sulphur or an imino group of the formula >N—$R_1$, wherein $R_1$ is hydrogen, a lower alkyl radical; a methylene group or a direct bond;

the compounds of formula I''':

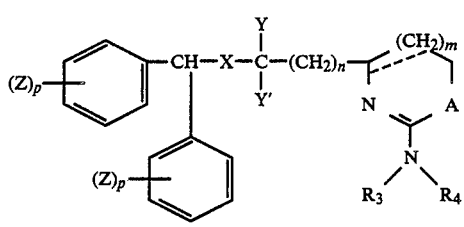

wherein the definitions of the substituents remain unaltered;

the compounds of formula I'''':

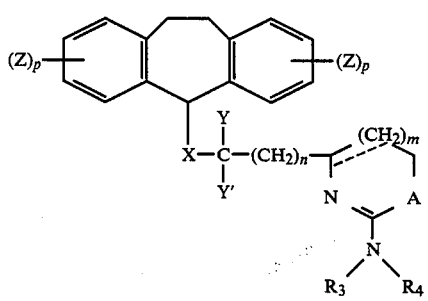

in which Z, X, Y, Y', $R_3$, $R_4$, A, m, $n_1$ and p have the same meaning as above-indicated;

and particularly the imidazolines of formula $I_A$:

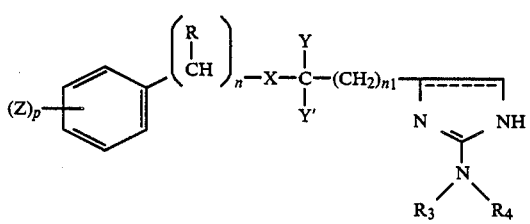

the tetrahydropyrimidines of formula $I_B$:

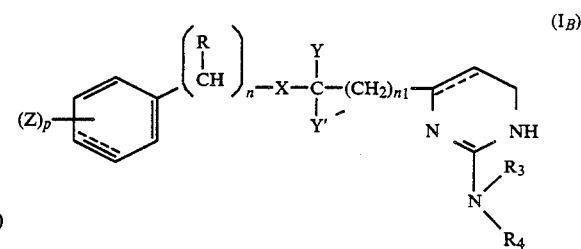

the 2-amino-thiazoles of formula $I_C$:

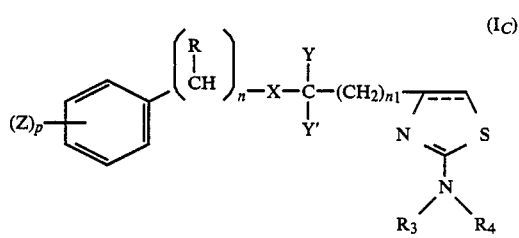

wherein the substituents Z, R, X, Y, Y', R, $R_3$, $R_4$, p, n and $n_1$ in the various formulas have the above-indicated definitions; as well as their acid addition salts with a mineral or organic acid.

Among the physiologically compatible acid addition salts, it may be cited the hydrochlorides, the hydrobromides, the sulphates, the nitrates, the phosphates, the sulfites, the acetates, the butyrates, the caproates, the suberates, the succinates, the tartarates, the citrates, the itaconates, the glutamates, the aspartates, the benzoates, the trimethoxy benzoates, the salicylates, the niflumates, the flufenamates, the mefenamates, the nicotinates, the isonicotinates, the benzene sulphonates, the methane sulphonates, the ethane sulphonates, the isethionates, the paratoluene sulphonates, the naphthalene sulphonates, the glucose-1-phosphates or the glucose 1,6-diphosphates.

The acids which may not be used for the therapy may be used as a means for isolating, pyrifying or resolving the compounds of formula I.

In this respect, it may be cited the perchlorates, the iodates, the bromates, the vanadates or the chromates; the salts with strychnic acid, d-chrysanthemic acid, indolyl-3-acetic acid, dichlorophenoxy isobutyric acid or citraconic acid.

As far as this invention is concerned, the word lower alkyl is intended to designate a hydrocarbon radical having from 1 to 6 carbon atoms in straight or branched chain. Examples of such radicals are the methyl, ethyl, isopropyl, sec-butyl, tert-butyl, neopentyl or n-hexyl.

A lower alkoxy radical includes an alkyl radical defined as above. Among the halogen atoms it may more particularly be cited the fluorine and chlorine. However, the bromo or iodo derivatives are about of the same interest.

A lower alkenyl radical is a hydrocarbon radical having a double bond, including from 2 to 6 carbon atoms. It may be cited as examples of lower alkenyl radicals, an allyl radical, a methallyl radical, a but-2-enyl radical, an isopropenyl radical or a 3-methyl but-1-enyl radical.

An alkylenedioxy radical has from 1 to 4 carbon atoms in the alkylene chain as for example methylenedioxy or ethylenedioxy.

When Y is a substituted phenyl radical, the substituents are one to three halogen atoms a trifluoromethyl radical or a trifluoromethoxy radical, one to three lower alkyl radicals or one to three lower alkoxy radicals.

When Y forms with the adjacent phenyl ring a bicyclic structure, the resulting compounds have the formula $I_E$:

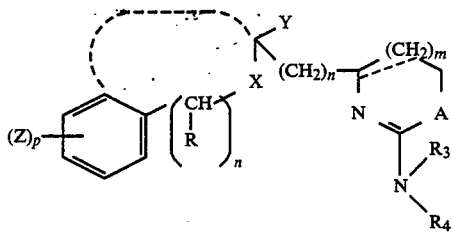

wherein:
X have the above-given definitions;
Y' is hydrogen or hydroxy; and
Z, $R_3$, $R_4$, A, m, n, p are defined as previously as examples of such bicyclic structures the compounds of formula:

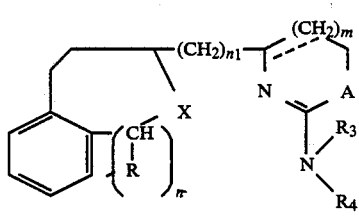

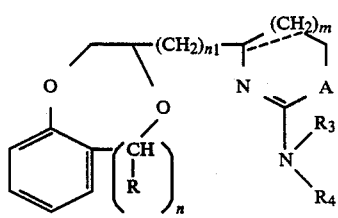

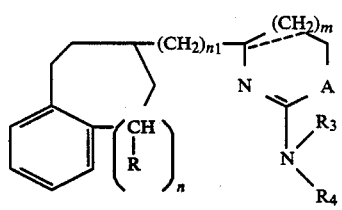

wherein X is oxygen, sulphur or $>N-R_1$ and n is 0 or 1.

Accordingly these bicyclic structures are those of benzodioxan tetrahydroquinoleines, tetrahydronaphthalene, dihydronaphthalene, or a benzimidazole.

These bicyclic structure may include further degree of insaturation such as for example a naphthyl-1, a naphthyl-2 ring.

An aryl lower alkyl radical is a mono cyclic aryl radical bearing a hydrocarbon chain having from 1 to 6 carbon atoms in straight or branched chain. Examples of such aryl lower alkyl radical are the benzyl, phenethyl, α-methylphenetyl, 2,6-dichlorobenzyl or 2,3,5-trimethoxybenzyl radicals.

A hetero aryl lower alkyl radical is a hetero cyclic aromatic radical bearing a hydrocarbon chain having from 1 to 6 carbon atoms. Examples of such radical are the pyridyl-2-methyl, the furyl-ethyl, the pyranylethyl or the thienyl-2 methyl radical.

When $R_3$ and $R_4$ are together an alkylene chain, the resulting cyclic structure has from 4 to 7 rings such as azetidine, pyrolidine, piperidine or hexamethylene imine. When this chain is interrupted by one or two extra hetero atoms, the resulting ring is for example a tetrahydropyrimidine, a tetrahydro-oxazine, a morpholine, a thiazine, a pyrazolidine or a piperazine ring. These rings may further be substituted such as with lower alkyl radicals hydroxy lower alkyl radicals, pyridyl, phenyl substituted phenyl radicals, or pyrimidyl.

When $R_3$ or $R_4$ is an acyl rasidue, it may derive from an aliphatic acid such as the acetyl radical, the propionyl, the dipropylacetyl radical; or from an aromatic acid such as the benzoyl, the naphthoyl-1, the 2,6-dichlorobenzoyl, the 3,4,5-trimethoxybenzoyl, the veratroyl, the syringoyl, the O-carbethoxy syringoyl, the nicotinoyl or the furoyl radicals; or from an aryloxy alkanoic acid such as phenoxy acetic acid, dichlorophenoxy acetic acid or p-chlorophenoxy isobutyric acid.

This invention also extends to a process for producing the compounds of formula I wherein m is equal to zero which consists in condensing an epihalohydrin of formula II:

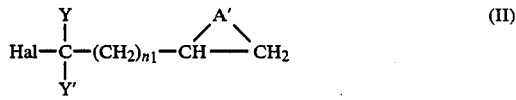

wherein:
A' is oxygen or sulphur; and
Hal is chlorine or bromine; and
the substituents Y, Y' and $n_1$ have the above given definitions, with an aromatic derivative of formula III:

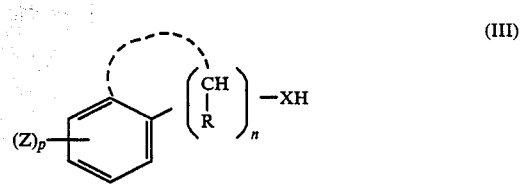

wherein the substituents R, Z, n, p and X are defined as previously given, producing an aryl alkylated derivative of the formula IV:

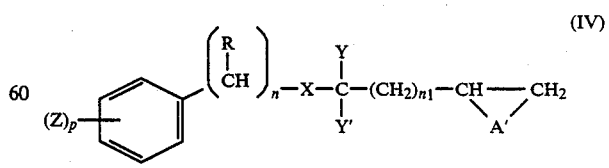

wherein the definitions of the substituents R, A', X, Y, Y', Z, n, $n_1$ and p remain unaltered, opening the oxiran ring by means of an alkali metal azide to produce the corresponding mono azide of formula V:

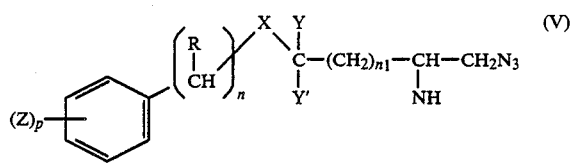

wherein the substituents R, A', X, Y, Y', Z, n, $n_1$ and p are defined as above given, submitting the latter when A is oxygen to the action of a functional derivative of a sulphonic acid of formula VI:

$$R_2SO_2R_5 \quad (VI)$$

wherein:

$R_2$ is a substituted or unsubstituted alkyl radical or a mono- or bicyclic aromatic radical; and $R_5$ is a lower alkyloxy group or a halogen atom, in the presence of a tertiary base to produce an azido ester of formula VII:

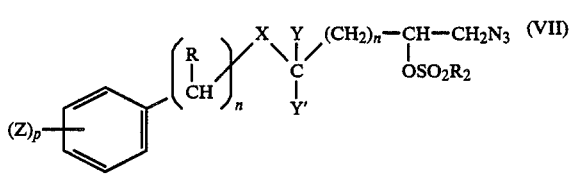

wherein the substituents X, Y, Y', Z, n, p and $R_2$ have the above-given definitions, reacting this ester with an alkali metal azide or thiocyanate in a polar solvent to obtain an azido derivative of formula VIII:

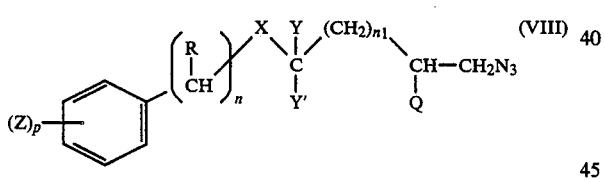

wherein:

the definition of the substituents R, X, Y, Y', Z, n, $n_1$ and p remain unaltered; and Q is a SH radical or an azido radical, which is reduced by hydrogenation in the presence of a catalyst to an amino ethane derivative of the formula IX:

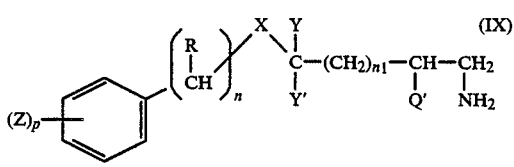

wherein:

the substituents R, X, Y, Y', Z, n, $n_1$ and p have the above given definitions; and Q' is a SH radical or an amino group, condensing the latter with a carbo iminating reagent selected from the group consisting of a cyanogene halide and a S-methyl isothiouronium halide of the formula:

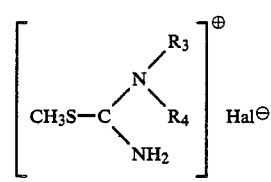

and recovering a compound of formula I wherein R, X, Y, Y', Z, n, $n_1$ and p have the above given definitions.

A is a sulphur or an imino radical and $R_3$ and $R_4$ are both hydrogen when the cyano iminating reagent is a cyanogen halide or $R_3$ and $R_4$ are hydrogen, and/or a lower alkyl, a lower alkenyl, an aryl lower alkyl, a hetero lower alkyl, an aryl, an alkoxy carbonyl or an acyl radical from an organic carboxylic acid having 1 to 10 carbon atoms or $R_3$ and $R_4$ are together with the nitrogen atom an alkylene chain, when the carbo iminating reagent is a S-methyl isothio uronium halide, which may be further salified by adding a mineral or organic acid or resolved into their optically-active isomers by reacting with a chiral reagent.

This invention also includes a process for preparing the compounds of formula I in which an aromatic derivative of formula V is condensed on allyl halide to produce an alkenylated compound of formula X:

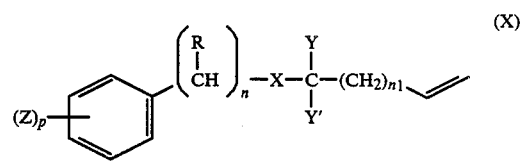

wherein Z, p, R, n, Y, Y' and $n_1$ are defined as above, brominating the latter with bromine to produce a dibromo derivative of formula XI:

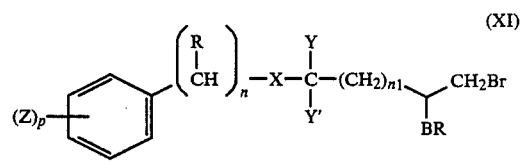

wherein Z, R, Y, Y', X, n, $n_1$ and p are defined as above reacting the latter with an alkali metal azide to produce the di-azido derivative of formula VIII:

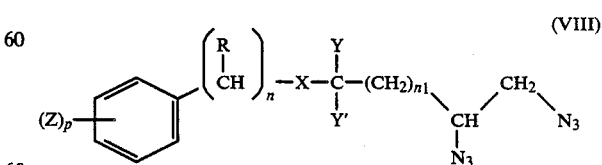

which is hydrogenated in the presence of a catalyst into a diamino derivative of formula IX:

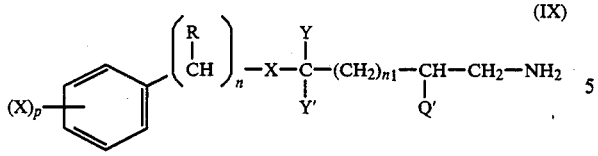

and cyclising this derivative by means of carbo iminating reagent such as a cyanogen bromide into a imidazolic derivative of formula $I_A$:

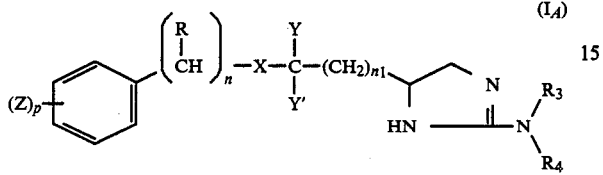

wherein the definitions of the substituents R, Z, X, Y, Y', $R_3$, $R_4$, n, $n_1$ and p are defined as above.

This invention further encompasses another process for producing the compounds of formula I which comprises:

(a) condensing an aryloxyalkyl aldehyde of formula XII:

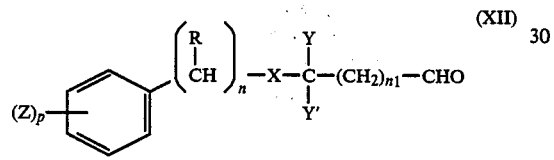

wherein the substituents R, X, Y, Y', Z, p and n are defined as above, with an alkali metal cyanide in the conditions of the Strecker's reaction to produce a α-cyano amine of the formula XIII:

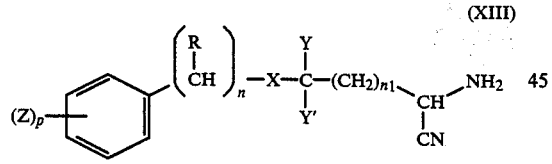

wherein the substituents R, Z, Y, Y', n, $n_1$ and p are defined as previously given;

(b) reducing the latter by hydrogenation in the presence of a catalyst into a substituted diamino ethane of formula IX:

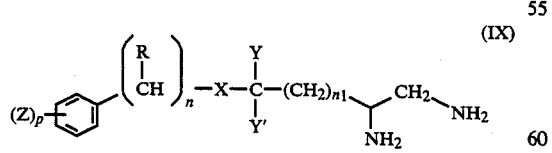

wherein the definitions of the substituents R, X, Y, Y', Z, n, $n_1$ and p remain unaltered;

(c) condensing this compound with a cyano iminating reagent to produce a cyclic derivative of formula $I_A$.

In order to produce a compound of formula I wherein $R_3$ and/or $R_4$ are an acyl radical, an alkyl radical, an alkenyl radical, an aryl radical or an aralkoyl radical, it may be used a process which comprises the steps of condensing a diamino ethane of formula IX:

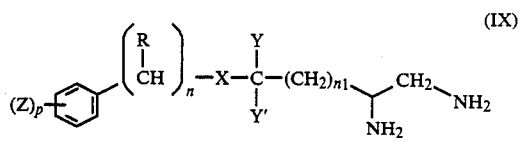

wherein the meanings of the substituents Z, p, R, X, Y, Y', n and $n_1$ remain those previously given with carbon disulfide to produce an imidazoline thione of formule XIV:

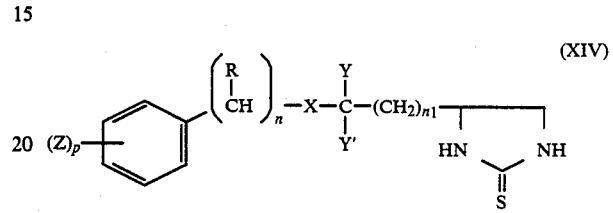

wherein the definitions given to the substituents Z, p, R, n, X, y, y' and $n_1$ remain unaltered, submitting the latter to an alkylating agent to produce an alkylthio imidazolinium salt of formula XV:

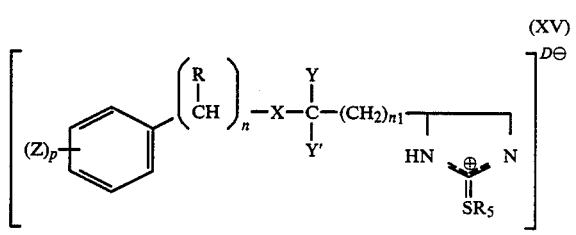

wherein:
the substituents keep the above given definitions $R_5$ is a lower alkyl radical; and D is mineral or organic anion, salifying the base condensing the latter with an amine of the formula XVI:

wherein $R_3$ and $R_4$ are defined as previously with the proviso they are not at the some time hydrogen, and producing a compound of formula $I_A$:

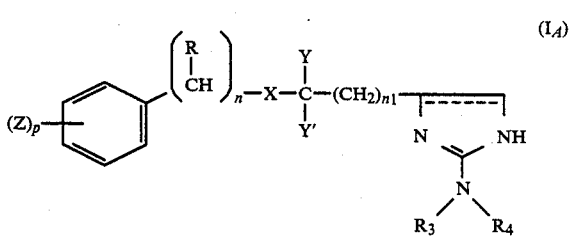

wherein:
$R_3$ is hydrogen, a lower alkyl radical, a lower alkenyl radical, an aryl lower alkyl radical, a (heteroaryl) lower alkyl radical, an aryl, an alkyloxy carbonyl group, an acyl radical derived from an organic carboxylic acid having from 1 to 10 carbon atoms;

$R_4$ is a lower alkyl radical, a lower alkenyl radical, an aryl lower alkyl radical, a (heteroaryl) lower alkyl radical, an aryl, an alkyloxycarbonyl, an acyl residue derivated from an organic carboxylic acid having from 1 to 10 carbon atoms; or $R_3$ and $R_4$ are together with the nitrogen atom to which they are bound, the alkylene chain of a heterocyclic ring, optionally including one or two further hetero atoms. To produce 2-acylamine derivatives of formula I, it may be also possible to let a functional derivative of an alkyl, aryl or arylalkyl carboxylic acid react with a 4,5-dihydro(1H)imidazole of formula XVII:

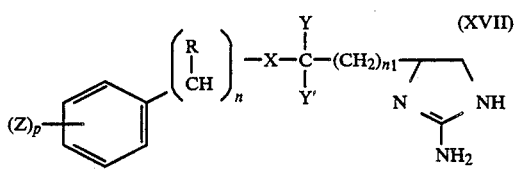

wherein the definitions of the substituents Z, p, R, n, X, Y, Y' and $n_1$ remain unaltered, according to the conditions of the Schotten-Baumann's reaction.

The compounds of formula $I_4$ wherein A is a group >NH and the dotted line symbolizes a double bond may be obtained according to a process which comprises the steps of oxydizing and 1-azido 3-aryloxy 2-propanol of formula V:

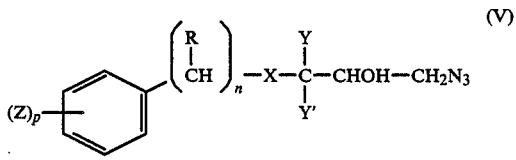

wherein:

Z, p, R, y, Y', R and n have the above given definitions; and

X is oxygen or sulphur or a radical >N—$R_1$ ($R_1$ being defined as previously), by means of a metallic oxydizing reagent in acidic medium to produce an azido ketone of formula XVIII:

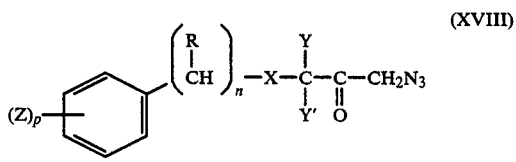

wherein Z, p, R, Y, Y', and X have the above-given definitions reducing the latter by catalytic hydrogenation into an amino ketone of formula XIX:

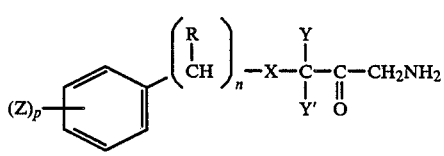

wherein the definitions of the substituents Z, p, R, n, X, Y, Y' remain unaltered, and condensing this ketone with cyanamid in the presence of an alkaline base to produce an imidazolinic derivative of formula $I_4$:

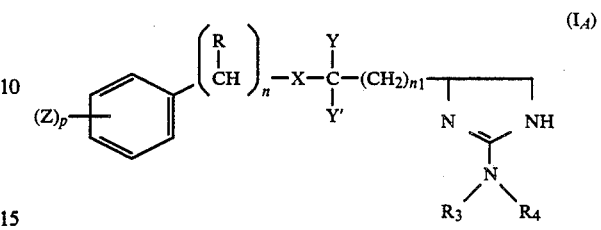

wherein the substituents Z, p, R, n, X, Y and Y' are defined as previously given, which may be salified by adding a mineral or organic acid or acylated by means of a functional derivative of an organic carboxylic acid, or resolved into its optically active isomers by means of an optically-active acid, or alkylated by means of alkylketone or an alkyl aldehyde in the presence of a reducing agent.

According to the most preferred features, the processes according to this invention may be defined as follows:

(1) The condensation of epihalohydrin of formula II with the aromatic derivative of formula III is carried out in a polar inert solvent such as for example acetonitide in the presence of a hydracid acceptor such as for example sodium, carbonate and potassium carbonate.

(2) The opening of the oxiran ring is performed by means of an alkali metal azide in an aqueous medium such as for example a mixture water-acetone, or a mixture water-acetonitrile or a mixture water-dimethyl formamide.

(3) The functional derivative of the sulphonic acid VI is preferably an alkyl sulphonyl halide such as methane sulphonyl chloride, ethane sulphonyl chloride, trifluoromethyl sulphonyl chloride; or an aryl sulphonyl halide such as for example benzene sulphonyl halide, p.toluene sulphonyl halide, or naphtylsulphonyl halide. The condensation is performed in the presence of a tertiary base such as triethyl amine, pyridine or collidine.

(4) The conversion of the sulphonate into an azide is performed in a polar aprotic solvent such as for example dimethylacetamide, dimethyl formamide, acetonitrile or hexamethyl phosphorotriamide.

(5) The hydrogenation of the azido or di-azido derivative is performed in the presence of a catalyst such palladium, or platum or an inert carrier such as charcoal, baryum sulphate, or strontium carbonate.

(6) The condensation of the aromatic derivative III with an allyl halide is performed in a polar solvent such as acetonitrile, in the presence of a basic reagent such as sodium carbonate or potassium carbonate.

(7) The bromation of the alkenylated derivative X is performed by means of bromine dissolved in an inert solvent such as for example carbon tetrachloride.

(8) The conversion of the dibrominated derivative into a diazido derivative is performed by heating the dibrominated derivative with an alkali metal azide in a polar solvent, such as dimethyl formamide or dimethyl sulfoxide.

(9) The cyclisation of the diaminated compound IX is performed by means of cyanogen bromide in an inert solvent such as an aromatic hydrocarbon at a temperature lower than 30°.

(10) The cyclisation of the diaminated IX is performed by means of a S-methyl isothio uronium halide, heating in an inert high boiling solvent such as isopropanol, propanol, collidine or xylene.

(11) The complete synthesis of the compounds of formula I may also be carried out starting from an already resolved raw material, coming from a natural product which has been conveniently transformed such as d-mennitol or 1-ascorbic acid.

Similarly, the epoxides of formula IV may be resolved into their geometric isomers and be converted by the further steps of the synthesis into the corresponding diastereoisomer.

The resolving agent is preferably an optically active acid such as d-tartaric acid, NN-diethyl d-tartranine acid, d-camphoric acid, 1-cetogulonic acid, abietic acid, pimaric acid or d-camphosulphonic acid.

It may also be used the physico-analytical means such as for example high pressure liquid chromatography (HPLC), or chromatography on a column filled with an optically-active carrier.

Moreover, it may be used for the resolution an enzymatic reagent such as amylase or a hydrolase, a hydroxy function being previously esterified. A hydroxy function may also be esterified by an optically-active acid such as d-camphonic acid, the epimeric esters thereof are separated then saponified into an optically active ester.

This invention also extends to the pharmaceutical compositions having as active ingredient at least one compound of formula I or an acid addition salt thereof with a mineral or organic acid in conjunction or admixture with an inert non-toxic pharmaceutically acceptable carrier or vehicle.

The pharmaceutical compositions may further incorporate another active ingredient having a synergistic or complementary action.

Preferably, the carrier or the vehicle is one of those suitable for the parenteral, oral, rectal sublingual, percutaneous or permucous way of administration.

Among the suitable pharmaceutical forms, it may more particularly be cited the uncoated or coated tablets, the dragees, the pills, the soft gelatine capsules, the cachets, the capsules, the injectable or drinkable solutions, the drinkable suspensions, the syrups, the suppositories, the solutions for percutaneous use, and the sublingual tablets. The carriers or vehicles are for example the starches, the celluloses or the chemical derivatives of cellulose such as ethyl cellulose or hydroxypropyl cellulose; carboxymethylamidon or the alkali metal salts thereof, magnesium phosphate, calcium carbonate, talc or magnesium stearate, water or saline solutions, syrup of suggar, syrup of arabic gum, cacao butter, polyethylene glycols, polyethylene glycol stearates.

The compounds of formula I and the salts thereof exhibit interesting pharmacological properties. They show namely anti-depressive properties and cardio-vascular properties due to some effects of the adrenergic type. More particularly the compounds of formula I and the salts thereof show positive inotropic and/or chronotropic effects. Moreover, some of them have antimicrobial and/or antiparasitic and/or antifungic properties against pathogene microbes or fungic or against noxious worms.

Accordingly, the compounds of formula I have a therapeutic use in human therapy as a drug for alleviating the acute or chronic cardiovascular failure more precisely in the shock conditions, and as a sypchotropic drug useful against the depressive conditions from endogenous or behavioural origin.

The useful dosology may vary depending the weight, the age of the patient, the route of administration and the therapeutic use. It ranges from 1 to 500 mg per unit dosage in the man and from 5 to 1,000 mg per day in the man.

This invention further relates to novel substituted 2-aminothiazoles and to processes for their manufacture.

More precisely it relates to novel 2-aminothiazoles the position 4 of which is substituted with an aryl alkyl substitution.

Specifically it provides the 4-arylalkyl 2-aminothiazoles of formula I:

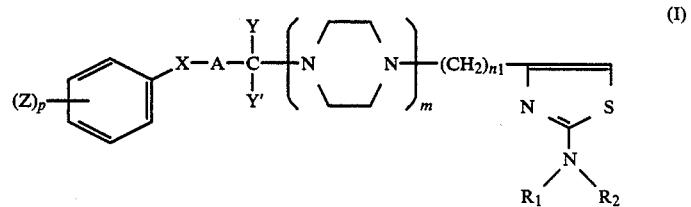

wherein:

Z is a substituent selected from the group consisting of hydrogen, halogen, a lower alkyl, a lower alkoxy, a (lower alkyl)thio, a trifluoromethyl, a trifluoromethoxy, a cyano, a nitro, an amino and a carboxamido;

X is an oxygen or a methylene;

A is a methylene or a direct bond;

Y and Y' are both hydrogen or together are the oxygen of a carbonyl group;

p is 1, 2 or 3;

m is zero or 1;

$n_1$ is zero, 1 or 2;

$R_1$ is hydrogen, a lower alkoxy carbonyl of the formula COOR wherein R is a lower alkyl radical, an aroyl group of the formula ArCO wherein Ar is phenyl or a substituted phenyl, the substituents of which are the same as Z, a lower alkoxy carbonyl, carbonyl group of the formula ROOC—CO— in which R has the previously given definitions;

$R_2$ is hydrogen, an aroyl group of the formula ArCO wherein Ar is defined as above, an acyl moiety from a lower alkyl carboxylic acid, or a lower alkyl sulphonic acid, an aryl sulphonic acid of the formula $ArSO_2$— wherein Ar has the above given meanings; or a lower alkyloxy carbonyl group.

This invention also provides the acid addition salts of a compound of formula I with a mineral or organic acid. Preferably the mineral or organic anion is derived from a therapeutically-compatible acid. Moreover if the anion is derived from an acid which cannot be used for a therapeutic purpose such as a perchlorate, a vanadate, a silicomolybdate, a silicotungstate, a chromate or a reineckate, the resulting salts may be used as identification or purification means. They may further be converted into the pure free base of formula I using a base or an anion-exchange resin.

Among the physiologically compatible acid addition salts, it may be cited the hydrochlorides, the hydrobromides, the sulphates, the nitrates, the phosphates, the sulfites, the acetates, the butyrates, the caproates, the suberates, the succinates, the tartarates, the citrates, the itaconates, the glutamates, the aspartates, the benzoates, the trimethoxy benzoates, the salicylates, the niflumates, the flufenamates, the mefenamates, the nicotinates, the isonicotinates, the benzene sulphonates, the methane sulphonates, the ethane sulphonates, the isethionates, the paratoluene sulphonates, the naphthalene sulphonates, the glucose-1-phosphates or the glucose 1,6-diphosphates.

According to this invention, the compounds of formula I have interesting antibacterial and antifungal properties. Precisely the compounds of formula I are active against Gram-positive such as Staphylococcus aureus or Steptococcus faecalis. They are also active against pathogenic fungi such as Candida albicans or Trich ophytum rubrum.

They found a use in human or veterinary therapy as antibacterial and/or antifungal medicines either by parenteral or oral way or by topic application locally on the site of infection.

They are particularly useful for treating the septicemias due to pathogenic staphylococci, the anginas due to Candida albicans and the cutaneous mycosis due to Trichophyton.

Among the compounds of formula I the most active are those in which Z is a halogen. For these compounds, p is 1 or preferably 1 or 3. They may be cited the following compounds:

4-[(2,4-dichlorophenoxy)methyl]2-NN-diethoxycarbonylaminothiazole;
4-[(2-chlorophenoxy)ethyl]2-aminothiazole;
4-[(4-chlorophenyl)ethyl]2-aminothiazole;
4-[(2,4-dichlorophenoxy)methyl]2-p.toluenesulphonylaminothiazole.

For the therapeutic purposes they are used in the form of pharmaceutical composition containing as active ingredient at least a compound of formula I or an acid addition salt thereof in conjunction or admixture with an inert non-toxic therapeutically-compatible carrier or vehicle.

Preferably the carrier or the vehicle is one of those suitable for the parenteral, oral, percutaneous or topic ways of administration.

The intended pharmaceutical compositions include the capsules, the soft gelatine capsules, the coated or non-coated tablets, the dragees, the pills, the sachets, the flavoured powders, the sweetened powders, the solutes or suspensions to be drunk, the creams, the lotions, the vaginal suppositories, the jellies and the sprays.

The usual dosology may range within extensive limits due to the low toxicity of the compounds of formula I and as a function of the route of administration, the nature of the disease, the severity of the infection and the localization of the infection. In general the dosology extends from 50 mg to 500 mg per unit dosage. In the man by oral way the daily doses range from 150 mg to 2,000 mg.

The compounds of formula I according to this invention are produced according to a process which comprises the steps of:

reacting a propenylated derivative of formula III:

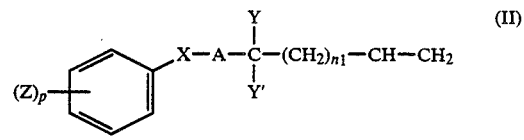

wherein Z, X, A, Y, Y', p and $n_1$ have the above-given meanings and m of the formula I is equal to zero, with a halogenating agent to produce the corresponding halohydrin of formual III:

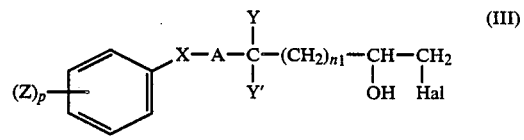

wherein:
Z, X, A, Y, Y', p and $n_1$ have the above-given definition; and Hal is a halogen other than fluorine;
oxydizing the latter with a metallic oxydizing reagent to produce the α-halogeno ketone of formula IV:

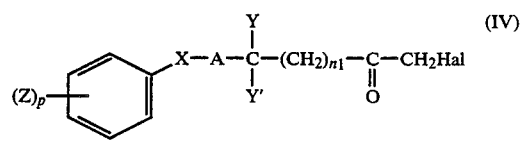

wherein:
Z, X, A, Y, Y', Hal, p and $n_1$ have the above-given meanings;
condensing this compound with thio urea in an inert oxygenated solvent to produce a 2-aminothiazole of formula I:

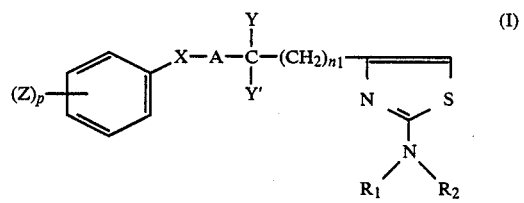

wherein:
$R_1$ and $R_2$ are both hydrogen; and
Z, X, A, Y, Y', $n_1$ and p have the above-given definitions.

The halohydrins of formula II may also be prepared according to the process which consists in reacting an aryl magnesium halide of the formula:

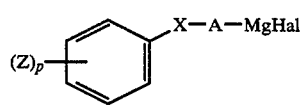

wherein:
Hal is a halogen other than fluorin; and
Z and p have the above-given definitions;

A is a methylene; and

X is an oxygen or a methylene, or X is a methylene and A is a direct bond, with an oxirane derivative of formula V:

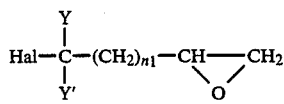

wherein Hal, Y, Y' and $n_1$ have the above-given definitions, and isolating the resulting halohydrin of formula:

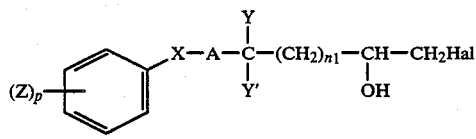

(III)

in which:

A is a methylene or a direct bond; and

Z, X, Y, Y', p and $n_1$ have the above-given definitions.

The compounds of formula I for which m is equal to one, i.e. the piperazinyl-substituted derivatives are prepared according to a process which comprises the step of condensing a (2-acylaminothiazolyl-4) lower alkyl halide of formula VI:

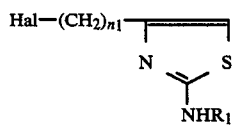

(VI)

wherein:

Hal has the above-given definition;

$n_1$ is one or two;

$R_1$ is a lower alkoxycarbonyl, an arylcarbonyl, a lower alkylcarbonyl or a lower alkylsulphonyl radical, with an arylpiperazine of formula VII:

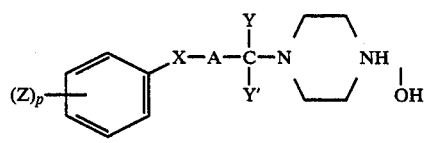

wherein the substituents Z, X, A, Y, Y' and p have the above-given definitions, in the presence of a basic reagent in a polar inert solvent, to produce the corresponding 2-aminothiazole of formula I:

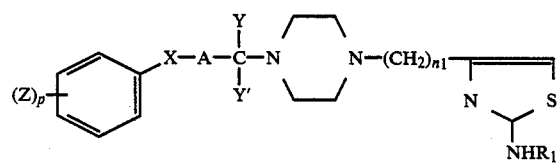

wherein Z, X, A, Y, Y', $R_1$ $n_1$ and p have the above given meanings.

When $R_1$ and/or $R_2$ are a hydrogen, they may be further acylated into a compound of formula I in which $R_1$ and/or $R_2$ are an acyl or lower alkoxycarbonyl moiety, by means of a functional derivative of a carbonic acid, carboxylic acid or sulphonic acid selected from the group consisting of a lower alkoxycarbonyl halide, a lower alkylcarboxylic halide, a lower alkylsulphonyl halide, an arylcarboxylic halide, an alkoxycarbonyl carbonyl halide.

Depending of the concentration of the acylating reagent it may be formed a mono acylated derivative having the partial formula:

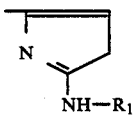

wherein $R_1$ is the above-defined acyl moiety, or a diacylated derivative having the partial formula:

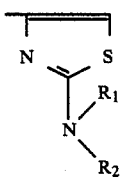

wherein $R_1$ and $R_2$ are both the above-defined acyl moieties.

EXAMPLE I 4-(O.chlorophenyloxymethyl) 2-amino 4, (-dihydro 1H Imidazole and its hydrobromide.

Step A. 1-O-chlorophenyloxy 2,3-epoxy propane/62,2 ml o.chlorophenol are dissolved in 500 ml acetonitrile and to this solution 248,4 g potassium carbonate and 0.5 g potassium iodide are added. After 30 mn stirring at room temperature, 140 ml epichlorhydrin are added dropwise. The whole mixture is heated to reflux for 15 hours. After the usual measures 60,1 g of a colourless liquid is recovered by distillation. It boils at 85° C. under $2.10^{-2}$ mm Hg.

Step B. 1.(o.chlorophenyloxy) 3-azido propopanol-2. To a solution of 51,7 g of epoxide of step A in 300 ml acetonitrile, 27.3 g sodium azide previously dissolved in 15 ml water are added. The mixture is heated to reflux for 4 hours. After the usual purifications, 61,17 g of a clear yellow liquid are obtained. The yield amounts to 96.4%. On silicat gel plates Rf=0.43 using a mixture toluene 9: tetrahydrofuran 1 as the eluting solvent.

Step C. 1-O.chlorophenyloxy 3-azido 2-tosyl oxypropane 61.17 g of the azide of step B are dissolved in 300 ml pyridine cooled to −10° and to this solution a solution of 66.7 g tosyl chloride in 300 ml pyridine is added for 1 hour while keeping the inner temperature between −5° C. and −2° C. The mixture is kept for 48 hours at 4° C. then poured on a mixture ice-water. The resulting precipitate is taken up in toluene and purified as usual. 90.1 g of a yellowish solid is obtained. Yield 87.4%. On silica gel plates Rf=0.63 using the mixture tetrahydrofuran 1/Toluene 9 as the eluting solvant.

Step D. 1-(O.chlorophenyloxy) 2,3-diazido propane. 9.3 g of the tosyloxy derivative of step C are dissolved in 30 ml dimethyl formamide and to this 3.9 g sodium azide are added. The mixture is kept under stirring for 30 mn at room temperature then 4 hours at 90° C. The resulting solution is poured in water and extracted with ether. After the usual purifications, 6.06 g of a slightly orange liquid are recovered. The yield amounts to 100%. On silica gel plates Rf=0.52 using the mixture petroleum ether 1/ethyl ether 1 as the eluting solvent.

Step E. 1-(O.chlorophenyloxy) 2,3-diamino propane. In a closed flask 49.77 of the diazido derivative, 250 ml ethanol and 10 g palladium on charcoal at 5% are added. The flask is purged by a stream of nitrogen then hydrogen is bubbled under strong stirring. The performance of the hydrogenation procedure is followed by TLC. The palladium on charcoal is thereafter filtered and 40.13 g of a brown coloured liquid are obtained. Purification is carried out by treatment with hydrochloric acid (dihydrochloride) then with base. 28 g of the free base of 1-(o.chlorophenyloxy methyl) 2,3-diamino propane are recovered. Yield: 70.8%.

Step F. 4-(O.chlorophenyloxymethyl) 2-amino 4,5-dihydro[1H]imidazole and its hydrobromide. To a solution of 11.32 g 1-(O.chlorophenyloxymethyl) 2,3-diaminopropane in 160 ml toluene one adds drop by drop a solution of 6.46 g cyanogene bromide in 60 ml toluene. The temperature must remain lower than 30° C. Stirring is kept for 5 hours at room temperature. After separation by filtration of the thus produced solid and usual purifications, 8.4 g of the pure hydrobromide are obtained as a colourless powder melting at 132° C. Yield=49%.

EXAMPLE II 4-(phenoxymethyl) 2-phenylamino 4,5-dihydro[1H]imidazole and its fumarate.

7 g of 1-phenoxy 2,3-diamino propane as the dihydrochloride, 8.55 g of S-methyl phenyl isothiouronium and 8.8 g triethylamine previously dissolved in 50 ml propanol are heated to 140° in a reactor for 12 hours. After usual purifications, a strongly coloured oil is recovered. It is purified by chromatography on a column filled with alumina and eluting after fixation with a mixture of methylene chloride 95—methanol 5—The eluates are treated with a solution of fumaric acid in ethanol giving rise to the formation of the fumarate which is purified by treatment with a mixture ethanol—ether—2.25 g of a colourless powder are thus obtained melting at 174° C. Yield=23%.

EXAMPLE III 4-benzyloxy 2-ethylamino 4,5-dihydro[1H]imidazole.

Step A: 3-benzyloxy prop 1-ene. To a mixture of 432 mg benzylic alcohol and 31.75 copper powder heated to 40°, 153 g redistalled allyl chloride are dropwise added. The mixture is kept at the reflux for 4 hours while adding some time to time sodium carbonate. After filtration to emiminate the mineral matters and usual purifications, the resulting liquid is chromatographied on a silica column. After fixation the desired product is eluted using the mixture petroleum ether 5—ethyl ether 95—66 g of the pure compound are thus obtained. Yield=44.6%.

Step B. 1-benzyloxy 2,3-dibromopropane. 162.5 g of 3-benzyloxyprop-1-ene are dissolved in 1000 ml carbon tetrachloride cooled to 0° and 56.5 ml bromine in 100 ml carbon tetrachloride are dropwise added while keeping the temperature at about 0°. After the usual measures, a yellow oily product is recovered and used as such for the next steps of the synthesis. The yield in raw product amounts to 98%.

Step C. 1-benzyloxy 2,3-diazidopropane. 50 g of the dibromo derivative of step B are dissolved in 300 ml dimethyl formamide and to this 26.4 g sodium azide are added. The whole mixture is kept under stirring for 12 hours while heating at 80°. Water is thereafter added and the residue is purified as usual. 31.45 g of an oily yellowish-coloured residue are recovered. The yield amounts to 83.5%.

Step D. 1-benzyloxy 2,3-diaminopropane. Using the method shown in example I step E and starting from 1-benzyloxy 2,3-diazido propane the 1-benzyloxy 2,3-diamino propane is obtained.

Step E. 4-benzyloxy 2-ethylamino 4,5-dihydro[1-H]imidazole and its hydrochloride. 7.5 g of 1-benzyloxy 2,3-diaminopropane as the dihydrochloride, 8.1 g of S-methyl ethyl isothio uronium iodide and 8.8 g triethylamine dissolved in 50 ml propanol are heated together at 140° on a reactor for 12 hours. After reversion to room temperature, the mixture is distilled off. The oily residue is purified by chromatography on silica gel column. The eluate is dissolved in 25 ml ether and saturated with a stream of hydrochloric acid. The hydrochloride progressively precipitates. It is kept for a night in a cool place then the crystals are separated which are dried and rinced with few ml of ether. After drying in an oven, 4.45 g 4-benzyloxy 2-ethylamino 4,5-dihydro[1H]imidazole are obtained as the hydrochloride.

EXAMPLE IV 4-(p. chlorobenzyloxymethyl) 2-(N-carbethoxy amino) 4,5-dihydro[1H]amidazole.

10 g of S-methylisothio Urea sulphate are dissolved in 8 ml water and 3.6 ml ethyl chloroformate are added thereto. The mixture is cooled to about 5° C. and 5.5 ml sodium hydroxide at 20% are added. The stirring is kept for 5 hours at room temperature. After usual purifications, the resulting compound as a pale yellow oil is added to 3.5 g 2,3-diamino 1-(p. chlorophenoxymethyl) propane as the hydrochloride and to 2.14 g sodium bicarbonate in 100 ml methanol. Methanol is distilled off then replaced with 150 ml n-propanol and the whole mixture is heated to reflux for 10 hours. The usual purifications supply with 2.17 g of a solid melting at 191° C. (hydrochloride). Yield=54%. All the described compounds have IR spectra and RMN spectra in accordance with the indicated structures.

EXAMPLE V 4-(benzodioxanyl-2) 2-amino imidazoline and its hydrobromide as well as their threo and erythro isomers.

Step A. 2-(benzodioxanyl-2) 2-hydroxy 1-azido ethane. Starting from 2-(benzodioxanyl-2) 2-hydroxy 1-bromo ethane and sodium stream dissolved in dimethyl formamide at a temperature of about 80° C., 2-(benzodioxanyl-2) 2-hydroxy 1-azidoethane is obtained.

Step B. Using the same procedure as in example I step C, starting from 2-(benzodioxanyl-2) 2-hydroxy 1-azido ethane and p. toluene sulphonyl chloride, 2-(benzodioxanyl-2)2-p. toluene sulphonyloxy 1-azido ethane is obtained.

Step C. Using the same procedure as in example I step D, 2-(benzodioxanyl-2) 2(p.toluene sulphonyloxy) 1-azido ethane is converted into 2-(benzodioxanyl-2) 1,2-diazido ethane which allows the separation of the isomers erythro and threo by chromatography on a column filled with silica.

Step D. Using the same procedure as in example V step E, and starting from 2-(benzodioxanyl-2) 1,2-diazido ethane as the mixture of isomers erythro and threo or in the resolved form-2-(benzodioxanyl-2) 1,2-diamino ethane is obtained.

Step E. Using the same procedure as in example I step F, and starting from 2-(benzodioxanyl-2) 1,2-diamino ethane and cyanogene bromide, 2-amino 4-(benzodioxanyl-2) imidazoline is obtained. This compound is further purified by converting it into its hydrobromide.

| MW | MP |
|---|---|
| (base) | (hydrobromide) |
| 219.25 | 225 |
| 219.25 | 180 |

| Theoretical | | | Analysis Found | | | |
|---|---|---|---|---|---|---|
| C | H | N % | C | H | N % | |
| 44.01 | 4.7 | 13.99 | 44.06 | 4.81 | 13.81 | isomers erythro |
| 44.01 | 4.7 | 13.99 | 43.89 | 4.82 | 13.72 | threo |

EXAMPLE VI

Using the same procedure as in example III, the following compounds have been prepared.

| (a) 4-(α-naphtyloxymethyl) 2-amino 4,5-dihydro [1H] imidazole as the hybromide MP = 175° C. MW of the base = 241.295 | | | | | |
|---|---|---|---|---|---|
| Theoretical | | | Found | | |
| C | H | N % | C | H | N % |
| 52.19 | 5.01 | 13.04 | 51.98 | 4.92 | 12.90 |

| (b) 4-(α-naphtyloxymethyl) 2-amino 4,5-dihydro [1H] imidazol melting at 194° C. as the hydrobromide. MW of the base = 241.295 | | | | | |
|---|---|---|---|---|---|
| Theoretical | | | Found | | |
| C | H | N % | C | H | N % |
| 52.19 | 2.01 | 13.04 | 52.32 | 5.11 | 12.99 |

| (c) 4-(2-methyl 4-bromophenoxy) 2-amino 4,5-dihydro [1H] imidazole. isolated as the hydrobromide melting at 190° C. | | |
|---|---|---|
| Analysis | | |
| C | H | N % |
| Theoretical 36.19 | 4.14 | 11.51 |
| Found 36.34 | 4.39 | 11.46 |

(d) 4-(2-methylphenoxy) 2-amino 4,5-dihydro [1H] imidazole isolated as the hydrobromide melting at 125° C.

EXAMPLE VII 4-(2,2-diphenylethyl-1) 2-amino[1H]4,5-dihydro imidazole.

This compound has been prepared starting from 4-4-diphenylbutl-ene previously described in the French Pat. No. 2.313.022, and converting it into the dibromo derivative, the diazido derivative, the diamino derivative, then cyclizing it by means of cyanogene bromide. This compound is obtained as the hydrobromide which melts at 175° C.

| Analysis: C₁₇H₁₉N₃,BrH = 265.31 | | | |
|---|---|---|---|
| | C | H | N % |
| Theoretical | 58.95 | 5.82 | 12.13 |
| Found | 59.11 | 5.95 | 12.10 |

EXAMPLE VIII

4-[(N-phenyl N-p.toluenesulphonylamino)methyl]2-amino[1H]4,5-dihydro Imidazole.

This compound is obtained starting from N-phenyl N-allyl p. toluene sulphonamide (described in Zhur. Organ. Khimii (1965) 918) through the dibromo derivative, the diazido derivative, the diamino derivative which is cyclized by means of cyanogene bromide. The imidazole is isolated as its hydrobromide which crystallizes with 5 mol water-MP=126°–127°

| Analysis: C₁₇H₁₉N₄SO₂,BrH,½OH₂ = 344.43 | | | |
|---|---|---|---|
| | C | H | N % |
| Theoretical | 47.01 | 5.10 | 12.89 |
| Found | 47.32 | 6.07 | 12.84 |
| | 47.45 | 5.98 | 12.82 |

EXAMPLE IX

[Dibenzo (a,d) [5H]10,11-dihydrocyclohepten-5 yl]4-methyl 2-amino[1H]4,5-dihydro imidazole.

This compound is obtained as its hydrobromide, starting from 5-allyl [dibenzo (a,d)[5H]10,11-dihydro cycloheptene] (described in the Belgian Pat. No. 633.597) and converting it into its dibromo derivative, its diazido derivative, its diamino derivative which is finally cyclized into the corresponding imidazole. The hydrobromide crystallizes with ⅓ mol water. MP higher than 55° then decomp.

| Analysis: C₁₉H₂₃N₃,BrH⅓H₂O = 291,41 | | | |
|---|---|---|---|
| | C | H | N % |
| Theoretical | 60.32 | 5.95 | 11.10 |
| Found | 60.48 | 5.96 | 11.22 |

EXAMPLE X

4-[(2-nitrophenoxy)phenyl methyl][1H]4,5-dihydro imidazole

This compound has been prepared starting from ethyl 2-nitrophenoxy 3-phenyl 2-hydroxy propionate (described in J. of Heterocyclic Chem 20 (1983) 259) which is hydrogenated to the corresponding diol, conversion of the latter to the dimethane sulphonate, then to the diazide and finally to the diamino derivative which is cyclized by means of cyanogene bromide. The hydrobromide melts at 237°.

EXAMPLE XI 4-phenoxymethyl 2-amino 1,4,5,6-tetrahydro pyrimidine.

Step A. 4-phenoxybutane 1,3-diol. 28 g (0,12 Mol) of ethyl 4-phenoxy 3-oxobutanoate are dissolved in 200 ml ethyl ether and to this solution it is added a suspension of 13.6 g lithium aluminohydride in 500 ml ethyl ether previously cooled to 0°. Sterring is kept for 2 hours at room temperature. The excess of reagent is destroyed by cautiously adding an aqueous solution of sodium sulphate. The precipitate is filtered and the filtrate is evaporated to dryness. The residue is taken up in petroleum ether from which it crystallizes. 20 g of the desired compound i.e. a yield of 92%. It melts at 52°-54°.

R M N spectrum (in CDCl$_3$) between 6.7 and 7.3. between 3.75 and 4

The diol is further converted into its ditosylate, then into the diazide, reduced into the diamino derivative and further cyclised in the tetrahydropyrimidine.

EXAMPLE XII 4-benzyl 2-amino[1H]4,5-dihydro imidazole the fumarate melts at 200°

| Anaylsis: C$_{10}$H$_{12}$N$_3$ = 231,257 | | | |
|---|---|---|---|
| | C | H | N % |
| Theoretical | 62.33 | 5.67 | 18.17 |
| Found | 62.10 | 5.62 | 18.00 |

EXAMPLE XIII 4-(O.chlorophenoxymethyl) 2-N-morpholino 4,5-dihydro[1H]imidazole Step A. 4-(o.chlorophenoxymethyl) 2-thio 4,5-dihydro[1H]imidazoline 0,2 mol of 3-O-chlorophenoxy 1,2-diamino propane are dissolved in 400 ml 80% ethanol. To this 12 ml carbon sulfide are dropwise added under a stream of argon. The mixture is heated to reflux for 1 hour. After reversion to room temperature 0.35 ml concentrated hydrochloric acid are added dropwise. The whole mixture is heated to reflux for 6 hours. After cooling an equal volume of water is added and the precipitate is separated. It is a yellow compound melting at 148°. It is purified by recrystallization from methylene chloride. Yield=52%.

Step B. 4-(O.chlorophenoxymethyl) 2-methyl thio imidazolinium hydro-iodide. To 0.08 mol of the compound of step A 6.25 ml (i.e. 14.2 g) of methyl iodide are added. The mixture is heated to the reflux for 1 hour then concentrated to dryness. The formed residue is washed with ether, then dried giving rise to the recovery of 29.3 g of a yellow compound which melts at 174° C. After recrystallization from isopropanol the melting point is increased to 175°. The yield amounts to 94%.

Step C. 4-(O.chlorophenoxymethyl) 2-N-morpholino 4,5-dihydro[1H]imidazole. 6 g of the hydro iodide of step B are added to 2.7 g of morpholine in 100 ml isopropanol. The mixture is heated to reflux for 24 hours. After evaporation of the solvent, the residue is taken up with water and the aqueous phase is washed with ether. 10% sodium hydroxyde is then added until the medium is neutral and the phase is extracted with methylene chloride. The methylene solution is washed with water dried and evaporated off. The compound is purified by converting it into its fumarate by adding fumaric acid in ethanol. The fumarate is recrystallised from methanol. It melts at 184° C. Yield=81%. Similarly the other N-substituted amino imidazolines are obtained reacting the S-methyl thio derivative with the suitable amines in a solvent such as isopropanol at the reflux or at a temperature ranging from 80° to 140° C. in a reactor.

EXAMPLE XIV 4-(O.chlorophenoxymethyl) 2-benzoylamino 4,5-dihydro[1H]imidazole.

To a solution of 6 g of 4-(O.chlorophenoxymethyl) 2-amino 4,5-dihydro[1H]imidazole in 200 ml water, a N-solution of sodium hydroxide is added to a pH value of 10.5. Under strong stirring a solution of benzoyl chloride in toluene (3.5 ml benzoyl chloride in 20 ml toluene) is added to. The addition is made drop by drop and lasts about 2 hours while adding at the same time a N-solution of sodium hydroxide in order to keep the pH value between 7 and 9.

A white solid separates and the stirring is kept for 5 further hours. The solid is filtered, washed with water then with toluene then with ethyl acetate.

It is recrystallized from ethanol. The 2-benzoylamino derivative melts at 213°. Yield=49.6%.

EXAMPLE XV 4-benzyl 2-amino thiazole.

10 g of 1-chloro 3-phenyl propan-2-one are added to 3.9 g thiourea in 100 ml ethanol. The mixture is refluxed for 2 hours. After cooling the whole is concentrated under reduced pressure. The residue is taken up in diluted ammonia then extracted with ether. After purifications the so obtained solid is converted into its hydrochloride which melts at 127°. The yield is=79%.

| Analysis: C$_{10}$H$_{10}$SN$_2$ = 190.27 | | | |
|---|---|---|---|
| | C | H | N % |
| Theoretical | 52.98 | 4.89 | 12.36 |
| Found | 52.58 | 4.96 | 12.30 |

In the same manner they have been prepared the following compounds:

—4—(phenoxymethyl) 2-amino thiazole its methane sulphonate melts at 153°.

| Analysis: C$_{11}$H$_{14}$N$_2$O$_4$S$_2$ = 302,37 | | | |
|---|---|---|---|
| | C | H | N % |
| Theoretical | 43.69 | 4.67 | 9.26 |
| Found | 43.86 | 4.78 | 9.20 |

4—(phenoxyethyl) 2-aminothiazole the hydrochloride of which, melts at 174°.

| Analysis: C$_{11}$H$_{13}$ClN$_2$OS = 256,75 | | | |
|---|---|---|---|
| | C | H | N % |
| Theoretical | 51.46 | 5.10 | 10.91 |
| Found | 51.36 | 5.21 | 10.98 |

EXAMPLE XVI 4-benzyl 2-benzoylaminethiazole

| Analysis: C$_{16}$H$_{15}$N$_2$ = 294.374 | | | |
|---|---|---|---|
| | C | H | N % |
| Calculated | 69.36 | 4.79 | 9.52 |
| Found | 69.45 | 4.90 | 9.42 |

MP=97°

4-(phenyloxymethyl)-2-p.chlorobenzoylaminothiazole MP=142°
4-(phenyloxymethyl)-2-propionylaminothiazole MP=135°
4-(phenyloxymethyl-2-dipropionylaminothiazole MP=64°
4-[(2-chlorophenyl)oxymethyl]-2-ethoxycarbonylaminothiazole MP=120°
4-[(2,4-dichlorophenyl)oxymethyl]-2-p.toluenesulphonylaminothiazole MP=186°
4-[(2,4-dichlorophenyl)oxymethyl]-2-diethoxycarbonylaminothiazole MP=63°
4-[(2,4-dichlorophenyl)oxymethyl]-2-propionylaminothiazole MP=140°
4-[(2,4-dichlorophenyl)oxymethyl]-2-ethoxycarbonylaminothiazole MP=151°
4-(2,4-dichlorophenoxymethyl)-2-ethoxalylaminothiazole MP=134°
4-(2,4-dichlorophenoxymethyl)-2-methylsulphonylaminothiazole MP=252°
4-(2,4-dichlorophenoxymethyl)-2-di(2,6-dichlorobenzoyl)aminothiazole MP=180°
4-(phenylpiperazinyl-1)-2-acetylaminothiazole (as the hydrochloride) MP=210°
4-[(4-methoxyphenyloxy)acetyl]-piperazinyl-1-methyl-2-acetylaminothiazole as the methanesulphonate
4-(phenylethyl)-2-aminothiazole as the hydrochloride MP=157°
4-(2-methoxybenzyl)-2-aminothiazole MP=160°
4-(2-chlorobenzyl)-2-aminothiazole as the hydrochloride MP=178°–180°
4-[(2-chlorophenyl)ethyl]-2-aminothiazole as the hydrochloride MP=166°
4-[(2-chlorophenoxy)ethyl]-2-aminothiazole as the hydrochloride MP=156°
4-[(4-chlorophenoxy)ethyl]-2-aminothiazole as the hydrochloride MP=152°
4-[(4-chlorophenyl)ethyl]-2-aminothiazole as the hydrochloride MP=185°

EXAMPLE XVII

Pharmacological study of the compounds of this invention

The compounds of formula I are endowed with an interesting pharmacological profile. (1) They exert more particularly antidepressive action, namely shown in the antagonist test of hypothermia and ptosis caused by reserpine, the test of hypothermia caused by apomorphine (the compounds of formula I are active at doses ranging from 50 to 200 mg/kg by oral way), and in the test of desperance in the mice (wherein the compounds are active at doses ranging from 20 to 40 mg/kg by intraperitoneal way). These anti-depressive effects of the compounds of formula I are not connected with any anti-cholinergic effect evidenced by their inactivity against the central or peripheric effects of Oxotremorine.

(2) Cardio vascular effects

In the cardio vascular field in the anesthetized dog, they exert hypertensive and positive inotropic and chronotropic actions of long duration with doses ranging from 0.1 to 1 mg/kg by intravenous way. They seemingly exert not any vaso constricting effect. These actions induce an increase in the cardiac output and the tissular perfusion. In the field of the cardio vascular shock experimentally produced for example by injection of endotoxin or platelet activating factor (PAF), the compounds of this invention at the doses herein above cited and by the same route of administration, antagonize the resulting cardio-vascular failure.

What is claimed is:

1. Novel 2-aminothiazole selected from the group consisting of
(a) a compound having the formula

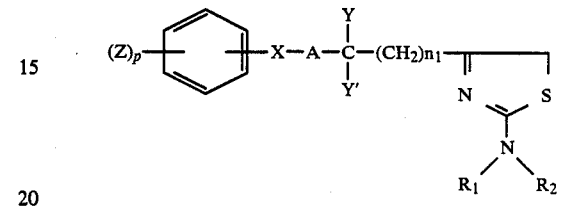

wherein
Z is a substituent selected from the group consisting of hydrogen, a halogen, a lower alkyl, a lower alkoxy, trifluoromethyl, trifluoromethoxy, cyano, nitro, carboxyamido, a lower alkenyl, a lower alkylthio and a lower alkylenedioxy;
X is an oxygen;
A is a methylene or a single bond;
Y and Y' are both hydrogen, or together are the oxygen of a carbonyl function;
$R_1$ and $R_2$ the same or different, are a substituent selected from the group consisting of hydrogen, a lower alkoxy carbonyl of the formula COOR wherein R is a lower alkyl radical, an acyl group of the formula ArCO wherein Ar is phenyl or a substituted phenyl wherein the substitutents are selected from the group consisting of 1 to 3 halogen atoms, trifluoromethyl, trifluoromethoxy, 1 to 3 lower alkyl radicals or one to three lower alkoxy radicals;
p is an integer of 1 to 3;
$n_1$ is zero, one or two; and
(b) the acid addition salts thereof.

2. The acid addition salts of a compound of claim 1.

3. A compound according to claim 1 which is 4-[(2,4-dichlorophenoxy)methyl]-2-NN-diethoxycarbonylaminothiazole.

4. A compound according to claim 1 which is 4-(2'-chlorophenoxy-ethyl)-2-aminothiazole.

5. A pharmaceutical composition having antibacterial and/or antifungal properties which incorporates as active ingredient an effective amount of at least one compound of claim 1 or acid addition salt thereof in admixture or conjuction with an inert non-toxic pharmaceutically compatible carrier or vehicle.

6. A pharmaceutical composition in accordance with claim 1, in which the amount of active ingredient ranges from 50 to 500 mg per unit dosage.

7. A method for treating the diseases due to bacterial infection in man or mammals which consists in administering to patients in need of such a therapy a safe but effective amount of a compound of claim 1 or an acid addition salt thereof.

* * * * *